United States Patent [19]
Steding

[11] Patent Number: 5,929,269
[45] Date of Patent: Jul. 27, 1999

[54] PROCESS FOR PREPARING VINYLATED ORGANOSILICON COMPOUNDS

[75] Inventor: Frank Steding, Riegestrasse, Germany

[73] Assignee: Huels Aktiengesellschaft, Marl, Germany

[21] Appl. No.: 08/853,452

[22] Filed: May 9, 1997

[30] Foreign Application Priority Data

May 11, 1996 [DE] Germany .......................... 196 19 138

[51] Int. Cl.⁶ ........................................................ C07F 7/04
[52] U.S. Cl. ............................................. 556/479; 528/15
[58] Field of Search ................................ 528/15; 556/479

[56] References Cited

U.S. PATENT DOCUMENTS

| | | | |
|---|---|---|---|
| 3,404,169 | 10/1968 | Gaignon | 556/479 |
| 3,793,358 | 2/1974 | Bauer | 556/479 |
| 4,276,426 | 6/1981 | Lindner | 556/479 |
| 4,898,961 | 2/1990 | Baile | 556/479 |

FOREIGN PATENT DOCUMENTS

| | | |
|---|---|---|
| 1 232 580 | 1/1967 | Germany . |
| 2 131 742 | 12/1972 | Germany . |
| 54122793 | 9/1979 | Japan . |

OTHER PUBLICATIONS

Bogdan Marciniec, et al., Applied Organometallic Chemistry, vol. 7, pp. 207–212, (1993), "Catalysis Of Hydrosilylation, Part XXII: Polymer–Protected Immobilized Platinum Complex Catalysts For Gas–Phase Hydrosilylation of Acetylene".

Dr.–Ing. O. Nagel, et al., Chemie–Ing.–Techn, vol. 42, pp. 474–479, (1970), "Strahldüsenreaktoren, Teil I: Die Anwendung Des Ejektorprinzips Zur Verbesserung Der Gasabsorptioin In Blasensäulen".

Dr.–Ing. O. Nagel, et al., Chemie–Ing.–Techn. vol. 42, pp. 921–926, (1970), "Strahldüsenreaktoren—Teil II: Stoffaustauschbeziehungen Für Die Gasabsorption Mit Chemischer Reaktion Bei Extremer Variation Der Filmdicke".

K. Hübner, Chemie Technik, vol. 16, No. 6, pp. 87–92, (1987), "Statische Und Dynamische Schlaufenmischer".

H.–J. Warnecke, et al., Chem.–Ing.–Tech., vol. 59, pp. 798–799, "Volumenbezogene Stoffübergangskoeffizienten Beim Strahldüen–Schlaufenreaktor".

Bogdan Marciniec, et. al., Applied Organometallic Chemistry, vol. 7, pp. 207–212, (1993), Catalysis of Hydrosylation, Part XXII: Polymer–Protected Immobilized Platinum Complex Catalysts for Gas–Phase Hydrosylation of Acetylene, 1993.

Primary Examiner—Melvyn I. Marquis
Assistant Examiner—Mark W. Milstead
Attorney, Agent, or Firm—Oblon, Spivak, McClelland, Maier & Neustadt, P.C.

[57] ABSTRACT

The present invention relates to a process for preparing organosilicon compounds which contain at least one $H_2C{=}CH{-}Si$-group, by reacting an organosilicon compound which contains at least one H—Si-group with acetylene in a gas/liquid phase in the presence of at least one addition catalyst and extracting the organosilicon compound which contains at least one $H_2C{=}H{-}Si$-group from the reaction mixture, wherein an organosilicon compound which contains at least one H—Si-group, the acetylene, which is used in stoichiometric excess, and a substantially inert liquid phase is brought into very intimate contact in a jet tube loop reactor in the presence of a catalyst, and the organosilicon compound which contains at least one $H_2C{=}CH{-}Si$-group is subsequently extracted from the reaction mixture and the excess acetylene is recycled into the process.

32 Claims, 1 Drawing Sheet

PROCESS FOR PREPARING VINYLATED ORGANOSILICON COMPOUNDS

BACKGROUND OF THE INVENTION

1. Field of the Invention

The invention relates to a process for preparing organosilicon compounds which contain at least one $H_2C=CH-Si$-group, by reacting an organosilicon compound which contains at least one H—Si-group with acetylene in a gas/liquid phase in the presence of at least one addition catalyst and extracting the organosilicon compound which contains at least one $H_2C=CH-Si$-group from the reaction mixture.

2. Discussion of the Background

It is known that vinylhalosilanes are obtained by acetylene being reacted, in the presence of a platinum catalyst, with a halosilane which contains 1 or 2 hydrogen atoms bound to the silicon and may or may not contain an inert univalent organic radical, if the reaction is carried out by heating, i.e. in a temperature range of from 80 to 120° C., in a liquid diluent and under atmospheric pressure. Thus German Patent No. 12 32 580 discloses that this process can be carried out discontinuously or continuously and that preferably only a slight excess of acetylene is used, based on the stoichiometric amount of the halosilane employed containing H—Si-bonds. Via this process, according to the examples of German Patent No. 12 32 580, product yields are achieved from around 80% up to 91%.

DE-A 21 31 742 teaches a process for the preparation of alkenylsilanes, by the addition of acetylene, which may or may not be substituted, to silanes being carried out in disilylethanes at from 120 to 220° C. and gauge pressures from 0.1 to 5.0 atmospheres, and the alkenylsilane obtained is removed continuously, as it is formed, and only as a gas from the reaction chamber. The preferred catalyst system used in this case comprises the reaction products of chloroplatinic(IV) acid with ketones.

The abovementioned processes have in common thy the addition of an acetylene to a silane which contains at least one H—Si-group takes place in tank reactors or reaction towers, one of the objectives having been to ensure a maximum mass transfer area and adequate residence times. Installations of these types are generally cost-intensive.

In more recent studies regarding the hydrosilylation of acetylene and trichlorosilane, immobilized platinum complex catalysts are used, yields of 80% being achieved with a selectivity of 100% for vinyl trichlolosilane; [Catalysis of hydrosilylation, Part XXII, *Applied Organometallic Chemistry* Vol 7 (1993), p. 207–212]. However, the preparation of such catalysts is comparatively complicated.

Another important economic aspect of the addition reactions in said processes involves the losses of acetylene which occur owing to unreacted amounts of acetylene, which as a rule are then removed from the process together with the waste gas and, for example, undergo thermal recycling in the form of a combustion plant.

It was an object of the present invention to provide a process via which organosilicon compounds which contain at least one $H_2C=CH-Si$-group can be prepared in a simple and economic way.

This object is achieved according to the invention in accordance with what is specified in the claims.

SUMMARY OF THE INVENTION

We have found that it is possible, by reacting an organosilicon compound which contains at least one H—Si-group with acetylene in a gas/liquid phase in the presence of at least one addition catalyst and extracting thee organo-silicon compound which contains at least one $H_2C=CH-Si$-group from the reaction mixture, for such an organosilicon compound which contains at least one $H_2C=CH-Si$-group to be prepared simply and economically, if an organosilicon compound which contains at least one H—Si-group, the acetylene, which is used in stoichiometric excess, and a substantially inert liquid phase are brought into very intimate contact in a jet tube loop reactor in the presence of a catalyst, and the organosilicon compound which contains at least one $H_2C=CH-Si$-group is subsequently extracted from the reaction mixture and the excess acetylene is recycled into the process.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
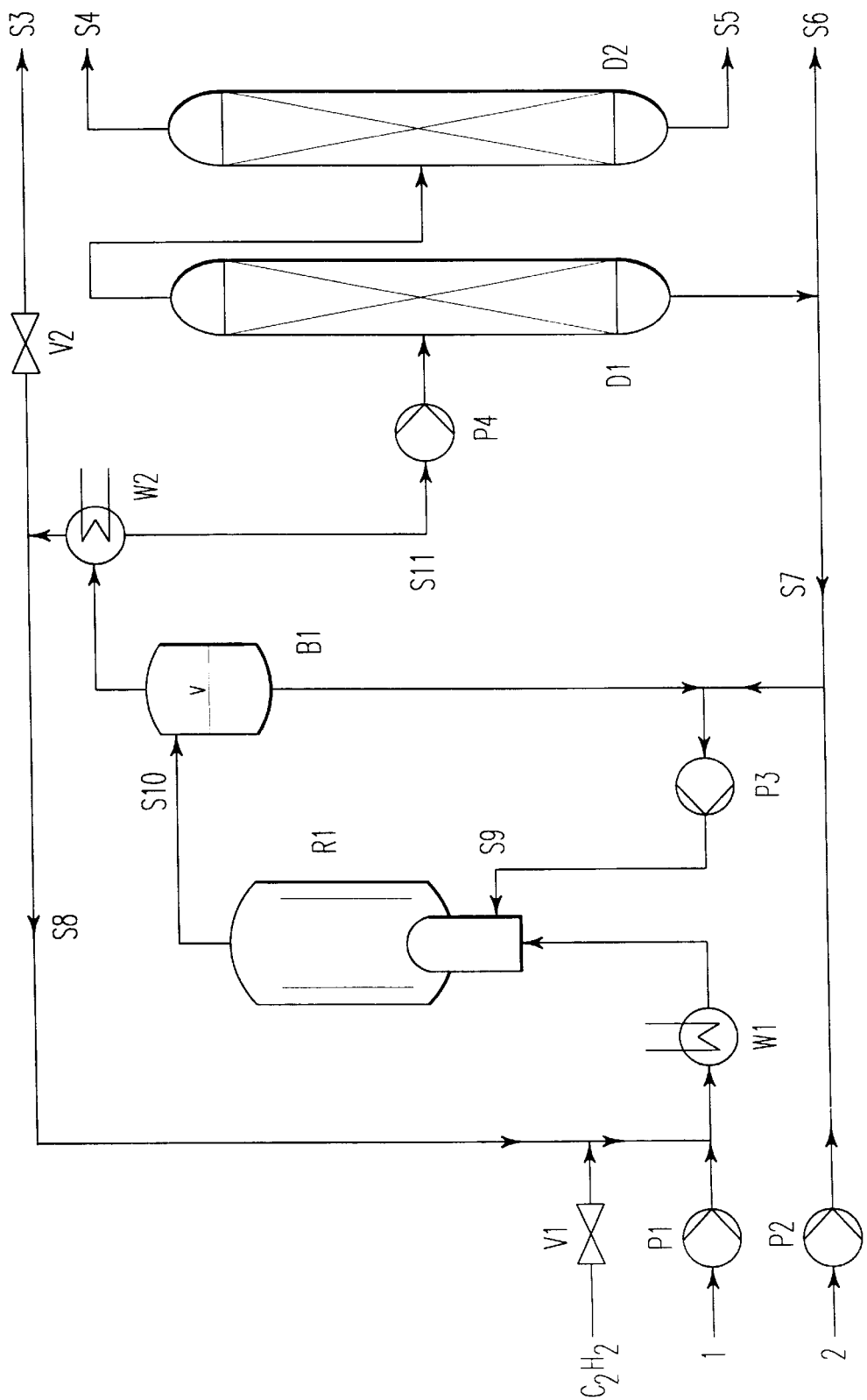
FIG. 1 shows a preferred embodiment of the process according to the invention.

In the present process, the use according to the invention of a jet tube loop reactor to prepare organosilicon compounds which contain at least one $H_2C=CH-Si$-group, ensures virtually optimal mass transfer and at the same time substantially mild reaction conditions, so that the process according to the invention achieves high selectivity, i.e. that undesirable side reactions and secondary reactions are largely avoided and high yields are achieved, in order for the process to be economically viable, The comparatively simple process according to the invention is thus distinguished by high spacetime yields, i.e. very high selectivities are achieved here at the same time as virtually 1 00% conversion with respect to the starting materials containing H—Si-groups.

Furthermore, the process according to the invention is particularly economical, since excess acetylene used can be recycled into the process and, moreover, the process can be operated even without employing a recycle gas compressor for acetylene recycling; in other words, as well as minimal acetylene losses, the present process provides the additional option, particularly in terms of economnics, of not investing into a recycle gas compressor.

The present invention therefore relates to a process for preparing organosilicon compounds which contain at least one $H_2C=CH-Si$-group, by reacting an organosilicon compound which contains at least one H—Si-group with acetylene in a gas/liquid phase in the presence of at least one addition catalyst and extracting the organosilicon compound which contains at least one $H_2C=CH-Si$-group from the reaction mixtre, wherein an organosilicon compound which contains at least one H—Si-group, the acetylene, which is used in stoichiometric excess, and a substantially inert liquid phase are brought into very intimate contact in a jet tube loop reactor in the presence of a catalyst, and said organosilicon compound which contains at least one $H_2C=CH-$Si-group is subsequently extracted from the reaction mixture and excess acetylene is recycled into the process.

Jet tube reactors or jet tube loop reactors whose use suitably extends to the process according to the invention, and their general mode of operation are described, inter alia, in the following literature references: Nagel et al. *CIT* 42 (1970), pp. 474–479, Nagel et al *CIT* 42 (1970), pp. 921–926, Hübner *CT* 16 (1987) pp. 87–92 Wamecke et at, *CIT* 59 (1987), pp. 798–799. A preferred embodiment of the reactor used in the process according to the invention is e.g. the jet tube loop reactor of type "System BURDOSA" from Burdosa, Germany, but types of identical or similar construction can also suitably be used.

The process according to the invention is generally carried out in such a way that the organosilicon compound which contains at least one H—Si-group is first fed into the jet tube loop reactor together with the acetylene and or with the liquid phase.

The operating pressure at which the acetylene is fed into the process is preferably >1 bar abs. and ≦1.4 bar abs.

In the process according to the invention, the organosilicon compounds employed which contain at least one H—Si-group are preferably have a purity of from 10 to 100% and those according to general formula I

$$R_aX_bH_{(4-a-b-c)}SiY_c \qquad (I)$$

where $R_a$ are each individually $C_{1-8}$ alkyl group, haloalkyl group, preferably containing F or Cl, and aryl group, for example phenyl, benzyl and naphthyl, X is Cl, OH, $C_{1-4}$ alkoxy group;

Y is —$((CH_2)_dSiR_2')_e(CH_2)_dSiR_3'$, where R' are each individually H, R and X;

where d is 1, 2, 3 or 4 and e is 0, 1 or 2;

a is 0, 1, 2 or 3;

b is 0, 1, 2 or 3; and c is 0 or 1, where (a+b+c):≦3.

For example hydrosilanes such as dimethylchlorosilane, methyldichlorosilane, dichlorosilane, 1,1,4,4-tetramethyldisilylethylene, trichlorosilane, or those according to the general formula II

$$R_aX_bH_{(3-a-b)}SiY \qquad (II)$$

where $R_a$ are each individually $C_{1-8}$ alkyl group, haloalkyl gri)up, preferably F or Cl, and aryl group, for example phenyl, benzyl and naphthyl;

X is Cl, OH, $C_{1-4}$ alkoxy group;

Y is (—O—$SiR_2'$)—O—$SiR_3'$, where R' are each individually H, R and X, and f=0, 1, 2, 3, 4 or 5;

a is 0, 1 or 2, and b is 0, 1 or 2, where (a+b)≦2.

Non-limiting examples of hydrosiloxanes are 1,1,3,3-tetramethyidisiloxane. Alternatively, hydrosilazanes, for example 1,1,3,3-tetramethyldisilazane, are suitable organosilicon compounds.

Alternatively, the organosilicon compounds are of the general formula III

$$[R_qX_rH_{(2-q-r)}SiO—]_s \qquad (III)$$

where $R_q$ are each individually a $C_{1-8}$ alkyl group, haloalkyl group, preferably containing F or Cl, and aryl group, for example phenyl, benzyl, naphthyl, X is Cl, OH, $C_{1-4}$ alkoxy group;

q is 0 or 1;

r is 0 or 1, where (q+r)≦1; and s is 3 or 4.

Non-limiting examples of cyclic hydrosiloxanes are 1,3, 5,7 tetramethylcyclotetrasiloxane.

In the process according to the invention, the organosilicon compound employed preferably is a starting material which comprises methyldichloro-silane or dimethylchlorosilane or mixtures thereof, or is dichlorosilane- or tetramethyidisiloxane.

In the process according to the invention, the molar ratio of acetylene to the respective organosilicon compound which contains at least cone H—Si-group is suitably set to a value of between 1.5:1 and 20.1.

Preferably, the organosilicon compound which contains at least one H—Si-group and the acetylene, prior to being fed into the jet tube loop reactor, is converted into a gaseous mixture. The gas or mixture present is generally drawn in via the mixing nozzle, is compressed to the system pressure and is mixed, in the mixing nozzle, with the liquid phase delivered. This liquid phase is suitably delivered to the mixing nozzle via a high-delivery pump. In the jet tube loop reactor, in particular in the loop region, the gas/mixture and the liquid phase can then be mixed very intimately. Suitably, the essentially inert liquid phase is preheated prior to being delivered into the jet tube loop reactor. In the process according to the invention, the jet tube loop reactor is operated, as a rule, at a temperature in the range of between 50 and 200° C., preferably between 70 and 140° C., the system pressure in the jet tube loop reactor suitably being between >1 bar abs. and 4 bar abs., preferably between 2 and 3 bar abs. The maximum system pressure is limited by safety considerations for handling acetylene under pressure at the respective temperatures. These limits do not correspond to the pressure/temperature limit curves relating to the spontaneous decomposition of acetylene.

The liquid phase used in the process according to the invention is suitably an essentially inert solvent or solvent mixture. Preferably, the respective solvent in the liquid phase has a higher boiling point than the organosilicon compound which is extracted from the reaction mixture and contains at least one $H_2C$=CH—Si-group. Suitable solvents include, for example, mesitylene, heat transfer oils, in particular tritoluene, such as e.g. MARLOTHERM®, but the liquid phase may also contain so-called called 'bis adducts" of the vinylation.

Both a heterogeneous and a homogeneous catalyst can be used as the addition catalyst in the process according to the invention. Examples of heterogeneous catalysts to be listed in this context include catalysts of the types as listed in German Patents Nos. 40 35 032 and 40 35 033. A heterogeneous catalyst in the process according to the invention is suitably placed within the jet tube loop reactor, for example as a fixed bed. The fixed bed may also include inert mixing elements and flow improvers. A homogeneous catalyst is suitably dissolved in the liquid phase employed in the present process. To have sufficient amounts of fresh homogeneous catalyst available for the reaction it may be necessary for solvent containing fresh catalyst to be fed back in during the process and for spent liquid phase to be discharged to the same extent. Platinum containing catalysts have proved particularly useful in the process according to the invention, though it is equally possible for other noble metal catalysts to be employed, for example Rh catalysts.

Downstream, the jet tube loop reactor may be connected, in the process according to the invention, to a condensation unit for the purpose of coarse separation of the reaction mixture (solvent/possibly "bis adduct"/possibly catalyst/ product and acetylene and possibly further similarly volatile components), with the option of the acetylene separated in the process being, recycled again as a starting material while pressure is maintained. Work-up of the reaction mixture, i.e.

of the crude product, to extract the organosilicon compound which contains at least one $H_2C=CH-Si$-group is generally carried out by distillation and the liquid phase which, in the process, accumulates in the bottom product is largely recycled into the process. The work-up by distillation in the process according to the invention can be carried out in a single-or multi-stage distillation, thin film evaporators and/or distillation columns, for example, being used for this purpose.

Another option in the process according to the invention is to work up the reaction mixture under reduced pressure. The present process thus provides the additional possibility of extracting monovinylated, divinylated and polyvinylated orgaliosilicon compounds, the process according to the invention generally being carried out continuously. The process may also be combined with a work-up of the catalyst to regenerate the catalyst and to recover the noble metal.

In accordance with the novel process it is possible to prepare organosilicon compounds such as e.g. vinylmethyldichlorosilane, vinyldimethylchlorosilane, divinyldichlorosilane, vinyl- and divinyltetramethyldisiloxane.

In the process according to the invention, overall process yields, based on the organosilicon compound employed, of from around 95 to 98% are generally achieved.

Having generally described this invention, a further understanding can be obtained by reference to certain specific examples which are provided herein for purposes of illustration only and are not intended to be limiting unless otherwise specified.

EXAMPLES

The abbreviations appearing in Example 1 refer to FIG. 1, where:
Plant sections:
R1 Jet tube loop reactor
B1 Plant section for separating the solvent (possibly together with catalyst and Si-containing by-products) from the crude product stream
P1 to P4 Pumps for conveying the material streams within the process
D1=Distillation column for distillation of crude product
D2=Distillation columnn for precision distillation
V1=Valve for adjusting the acetylene supply
V2=Valve for adjusting the residual-gas flow rate
W1=Heat exchanger including mixing section
W2=Condensation unit for separating the unconsumed acetylene from the crude product
Material streams:
$C_2H_2$=Acetylene supply
S1=Organosilicon compound containing at least one H—Si-group
S2=Supply of dissolved or suspended fresh catalyst
S3=Residual-gas outlet
S4=Top product of column D2
S5=Bottom product of column D2
S6=Outlet for excess bottom product of column D1
S7=Solvent recycle
S8=Acetylene recycle stream
S9=Solvent cycle
S10=Two-phase stream acetylene/reaction product
S11=Product feed to distillation.

EXAMPLE 1

A jet tube loop reactor (R1) operated in continuous mode is fed with 0.8 mol/h of liquid methyldichlorosilane (S1) via the pump (P1) and the evaporator (W1), together with fresh acetylene ($C_2H_2$). Prior to entering the evaporator, the fresh acetylene is mixed with the acetylene recycle stream (S8).

The reaction temperature is 80° C., the pressure 1.5 bar abs. At the same time, a solvent cycle (S9) of about 80 l/h is operated via the recirculation pump (P3) and, prior to entering the jet nozzle (R1) is compressed to about 10 bar abs.

Leaving the reactor (R1) is a two-phase stream (S10) which consists of the excess actylene and the liquid reaction product. The concentration of vinylmethyldichlorosilane is about 15 wt %.

In the phase separator (B1), acetylene and the product mixture, which consists of the desired vinylsilane and fore-run and tailings components, are separated from the solvent. The solvent returns to the solvent cycle (S9) via the pump (P3).

In the condenser (W2) the product mixture is condensed and is supplied, via the pump (P4), as a feed (S11) to the distillation column (D1). The excess acetylene is passed back into the reactor via the cycle (S8). The system pressure in the reactor(R1) is controlled via the valve (V2). Residual gas leaves the plant via the residual-gas outlet (S3).

From the bottom of the column (D1) entrained solvent and high-boiling components, e.g. "bis adduct" (1,4-dimethyl-1,1,4,4-tetrachloro-1,2-disilane) formed in the reaction are fed into the solvent cycle via the solvent recycle (S7). High-boiling components originating from the reaction, e.g. "bis adducts" can be removed, together with solvent, via the stream (S6). The vinylsilane is drawn from the bottom (S5) of the column (D2) in highly pure form.

The reactor is started up with pure solvent, in this case mesitylene. The catalyst employed is a conventional, homogeneously dissolved hydrosilylation catalyst based on $H_2PtCl_6$. The Pt concentration is about 3 ppm. The supply of catalyst/solvent (S2) is effected via the pump (P2).

If the plant is operated continuously, the solvent is diluted by high-boiling reaction products, e.g. "bis adduct". The selectivity of the vinylation is not adversely affected by the increase in high-boiling components.

Given a silane conversion of 99% of methyldichlorosilane, a yield in terms of vinylmethyldichlorosilane of 97% can be achieved by the process

EXAMPLE 2

In the equipment according to Example 1, a mixture of 70 mol % of methyldichlorosilane and 30 mol % of isopentane is used, the same procedure being followed as described in Example 1. The silane throughput is 0.8 mol/h, the acetylene stream 1 mol/h. Given a silane conversion of 98%, a yield of 97% in terms of vinylmethyldichlorosilane can be achieved.

EXAMPLE 3

Dimethylchlorosilane is employed in the equipment according to Example 1. The silane throughput is 1 mol/h, the acetylene stream 1.2 mol/h. The reaction temperature is 92° C. Given a silane conversion of 99.8%, a selectivity of 98% for vinyldimethylchlorosilane is achieved.

Obviously, numerous modifications and variations of the present invention are possible in light of the above teachings. It is therefore to be understood that within the scope of the appended claims, the invention may be practiced otherwise than as specifically described herein.

This application is based on German patent application 196 19 138.6 filed in the German Patent Office on May 11, 1996 the entire contents of which are hereby incorporated by reference.

What is claimed as new and desired to be secured by Letters Patent of the United States is:

1. A process for preparing an organosilicon compound product which contain at least one $H_2C=CH-Si$-group, comprising reacting an organosilicon compound reactant which contains at least one H—Si-group with acetylene in a gas/liquid phase in the presence of at least one addition catalyst and extracting said organosilicon compound product which contains at least one $H_2C=CH-Si$-group from the reaction mixture, wherein said organosilicon compound reactant and said acetylene in gas phase and a substantially inert liquid phase are brought into very intimate contact in a jet tube loop reactor in the presence of a catalyst, and said organosilicon compound product is subsequently extracted from the reaction mixture and excess acetylene is recycled into said process, wherein said acetylene is used in stoichiometric excess.

2. The process of claim 1, wherein said organosilicon compound reactant is fed into said jet tube loop reactor together with said acetylene and/or with said liquid phase.

3. The process of claim 1, wherein said organosilicon compound reactant and said acetylene, prior to being fed into said jet tube loop reactor, are converted into a gaseous mixture.

4. The process of claim 1, wherein said substantially inert liquid phase is preheated before being fed into said jet tube loop reactor.

5. The process of claim 1, wherein said jet tube loop reactor is operated at a temperature in the range of between 50 and 200° C.

6. The process of claim 1, wherein said acetylene is fed into the process at an operating pressure of >1 bar abs. and ≦1.4 bar abs.

7. The process of claim 1, wherein said jet tube loop reactor is operated at a system pressure of between >1 bar abs. and the maximum permitted pressure as defined by GMP for acetylene at the reaction temperature, preferably at between 1 and 3 bar abs.

8. The process of claim 1, wherein said liquid phase used is a substantially inert solvent or solvent mixture.

9. The process as claimed in claim 8, wherein said substantially inert solvent or solvent mixture in said liquid phase has a higher boiling point than said organosilicon compound reactant.

10. The process of claim 8, wherein said substantially inert solvent is mesitylene.

11. The process of claim 8, wherein said substantially inert solvent comprises inert heat transfer oils.

12. The process of claim 8, wherein a homogeneous catalyst is employed.

13. The process of claim 12, wherein said homogeneous catalyst is dissolved in said liquid phase.

14. The process of claim 1, wherein a heterogeneous catalyst is employed.

15. The process of claim 14, wherein said heterogeneous catalyst is placed in said jet tube loop reactor.

16. The process of claim 1, wherein a platinum-containing catalyst is employed.

17. The process of claim 1, wherein said organosilicon compound reactant is a hydrosilane of the general formula I

  (I)

where $R_a$ are each individually a $C_{1-8}$ alkyl group, a haloalkyl group, or an aryl group;

X is Cl, OH, $C_{1-4}$ alkoxy group;

Y is $-((CH_2)_d SiR_2')_e(CH_2)_d SiR_3'$, where R' are each individually H, R or X;

where d is 1, 2, 3 or 4 and e is 0, 1 or 2;

a is 0, 1, 2 or 3;

b is 0, 1, 2 or 3; and c is 0 or 1, where (a+b+c)≦3 or a hydrosilane of the general formula II

  (II)

where $R_a$ are each individually a $C_{1-8}$ alkyl group, a haloalkyl group, or an aryl group;

X is Cl, OH, $C_{1-4}$ alkoxy group;

Y is $(-O-SiR_2')-O-SiR_3'$, where R' are each individually H, R or X, and f=0, 1, 2, 3, 4 or 5;

a is 0, 1 or 2, and b is 0, 1 or 2, where (a+b)≦2, or a cyclic hydrosiloxane of the general formula III

  (III)

where $R_q$ are each individually a $C_{1-8}$ alkyl group, a haloalkyl group, or an aryl group;

X is Cl, OH, $C_{1-4}$ alkoxy group;

q is 0 or 1;

r is 0 or 1, where (q+r)≦1; and s is 3 or 4.

18. The process of claim 1, wherein said organosilicon compound reactant comprises methyldichlorosilane or dimethylchlorosilane or mixtures thereof, or is dichlorosilane or tetramethyldisiloxane.

19. The process of claim 1, wherein said organosilicon compound reactant is of a purity of from 10 to 100%.

20. The process of claim 1, wherein a molar ratio of acetylene to said organosilicon compound reactant which contains at least one H—Si-group is set to a value of between 1.5:1 and 20:1.

21. The process of claim 1, wherein extracting of said reaction mixture to extract said organosilicon compound reactant is carried out by distillation and said liquid phase which, in the process, accumulates in the bottom product is largely recycled into said process.

22. The process of claim 21, wherein said extracting by distillation is carried out in a single- or multi-stage distillation.

23. The process of claim 22, wherein said extracting by distillation employs thin-film evaporators and/or distillation columns.

24. The process of claim 1, wherein a monovinylated organosilicon compound is extracted.

25. The process of claim 1, wherein a divinylated organosilicon compound is extracted.

26. The process of claim 1, wherein a polyvinylated organosilicon compound is extracted.

27. The process of claim 1, wherein said extracting of said reaction mixture is carried out under reduced pressure.

28. The process of claim 1, wherein said process is operated continuously.

29. The process of claim 1, wherein said jet tube loop reactor is operated at a temperature in the range of between 70 and 140° C.

30. The process of claim 11, wherein said substantially inert solvent comprises tritoluene.

31. The process of claim 17 wherein said haloalkyl group contains F or Cl.

32. The process of claim 17, where said aryl group is selected from the group consisting of phenyl, benzyl and naphthyl.

* * * * *